US009440934B1

(12) United States Patent
Mehta et al.

(10) Patent No.: US 9,440,934 B1
(45) Date of Patent: Sep. 13, 2016

(54) SYNTHESIS OF COPPER(I) 5-NITROTETRAZOLATE

(71) Applicants: Neha Mehta, Succasunna, NJ (US); Karl Oyler, New York, NY (US); Gartung Cheng, Edison, NJ (US); Jerry Salan, Salem, CT (US); Shannon Lenahan, Ivorytown, CT (US)

(72) Inventors: Neha Mehta, Succasunna, NJ (US); Karl Oyler, New York, NY (US); Gartung Cheng, Edison, NJ (US); Jerry Salan, Salem, CT (US); Shannon Lenahan, Ivorytown, CT (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/628,753

(22) Filed: Feb. 23, 2015

Related U.S. Application Data

(60) Provisional application No. 61/977,770, filed on Apr. 10, 2014.

(51) Int. Cl.
| | |
|---|---|
| *C07D 257/06* | (2006.01) |
| *C07D 257/04* | (2006.01) |
| *C07D 271/12* | (2006.01) |

(52) U.S. Cl.
CPC ........... *C07D 257/06* (2013.01); *C07D 257/04* (2013.01); *C07D 271/12* (2013.01)

(58) Field of Classification Search
CPC .... C06C 7/00; C07D 257/06; C07D 257/04; C07D 271/12; C06B 49/00; C06B 41/00; C06B 25/04; C06B 33/00; C06B 41/02; C06B 41/06; C06B 23/00; C06B 31/38; C06B 31/42; C06B 33/12; C06B 35/00; C06B 43/00; C06B 45/22; C06B 47/14
USPC .......................................... 548/250, 251, 253
See application file for complete search history.

(56) References Cited

U.S. PATENT DOCUMENTS

| | | | | |
|---|---|---|---|---|
| 2,066,954 | A | * | 1/1937 | Von Herz ...................... 548/109 |
| 3,965,951 | A | * | 6/1976 | Scott et al. ...................... 149/23 |
| 4,093,623 | A | * | 6/1978 | Gilligan et al. .............. 548/109 |
| 8,523,989 | B2 | | 9/2013 | Fronabarger |

OTHER PUBLICATIONS

Ford et al. "Development of a Lean Process to the Lead-Free Primary Explosive DBX-1" Org. Process. Res. Dev. 2015, 19, 673-680.*
Klapotke et al. Z. Anorg, Allg. Chem. 2013, 639, 681-688.*
Klapotke et al. Inorg. Chem. 2008, 47, 6014-6027.*
Zaborenko et al. Ind. Eng. Chem Res. 2010, 49, 4132-4139.*
Klapotke et al. Dalton Trans. 2009, 1983-1841.*
Fronabarger, John W., et al., DBX-1—A Lead Free Replacement for Lead Azide, Propellants, Explosives, Pyrotechnics, 2011, 541-550, vol. 36, Wiley Online.

\* cited by examiner

*Primary Examiner* — Nyeemah A Grazier
*Assistant Examiner* — Amanda L Aguirre
(74) *Attorney, Agent, or Firm* — Lisa H. Wang

(57) ABSTRACT

A method of manufacture of the primary explosive material copper(I) 5-nitrotetazolate (DBX-1) by a synthesis starting with 5-aminotetrazolate (5-AT); wherein, the synthesis provides intermediates acid copper salt of 5-NT and sodium 5-nitrotetazolate (NaNT) sodium 5-nitrotetazolate (NaNT)—that are both, free of any 5-aminotetrazolate (5-AT) starting material—such that the subsequent production of the DBX-1 is not inhibited. Further, this method utilizes an internal filter within the reactor—to minimize handling of explosively dangerous intermediates.

12 Claims, 4 Drawing Sheets

Schematic Representation of Present Invention Method Steps

For the Conversion of 5-AT to NaNT

Step 6
1. Transfer to Reactor 2
2. Add copper(II)chloride
3. Add DBX-1 seed
4. Dose sodium Ascorbate
5. DBX-1 forms

Step 7
1. Stop agitation
2. Solids Settle
3. Lower filter
4. Remove liquors

Step 8
1. Add water wash
2. Agitate
3. Stop Agitation
4. Solids Settle
5. Lower filter
6. Remove wash

Step 9
1. Filter solid DBX-1
2. Packout solids

FIG 2

Schematic Representation of Present Invention Method Steps

For the Conversion of NaNT to DBX-1

Schematic Representation of Present Invention Method Step

For Internal Filtration of Complex 1

Schematic Representation of Present Invention Method Step

For Internal Filtration of DBX-1

SYNTHESIS OF COPPER(I) 5-NITROTETRAZOLATE

CROSS REFERENCE TO RELATED APPLICATIONS

This application claims the benefit under 35 USC §119(e) of U.S. provisional patent application US 61/977,770, filed 10 Apr. 2014, which provisional is hereby incorporated by reference herein.

FEDERAL RESEARCH STATEMENT

The inventions described herein may be manufactured, used and licensed by, or for the U.S. Government, for U.S. Government purposes.

BACKGROUND OF INVENTION

1. Field of the Invention

The present invention relates to a safer and more efficient method of synthesizing the primary detonator material copper(I) 5-nitrotetrazolate (DBX-1) starting with 5-aminotetrazole (5-AT); wherein, the intermediate materials of an acid copper salt of 5-nitrotetrazol (5-NT) and sodium 5-nitrotetrazolate (NaNT) are free of the starting material 5-AT—a material which inhibits the formation of the DBX-1.

2. Related Art

In military and commercial blasting, the explosive chain reaction is typically initiated by detonation of a small quantity of a highly sensitive primary explosive material. The sensitive nature and significant explosive effect of such primary explosive materials, allows for significantly larger quantities of relatively insensitive secondary high explosive material to be detonated using a very small quantity of the very sensitive primary explosive material—thereby minimizing the overall sensitivity of the explosive system. Two of the most widely used primary explosives are lead(II) azide ("LA") and lead(II) styphnate—which, due to their lead content, have significantly contaminated the air and soil about military training grounds and government and commercial firing ranges—posing a hazard to the safety of the personnel working thereabout, as well as, the environment in general. In addition, LA is problematic because the azide anions can react with moisture in the presence of carbon dioxide to generate hydrazoic acid, a toxic and explosive material. Further, azide can also form extremely sensitive explosive complexes with other metals, such as copper. The unintended formation of copper azides in aging munitions with copper detonator shells has let to fatal accidents as bomb investigators and explosive ordinance disposal teams have attempted to move such items.

Considering the above drawbacks of LA and lead(II) styphnate, as detailed above, there has been a focus on developing alternative minimally toxic and chemically inert primary explosives. One promising alternative primary explosive material is copper(I) 5-nitrotetrazolate (aka "DBX-1")—which has proven to be a drop-in replacement for LA in existing detonator designs. DBX-1 has comparable properties to LA as an explosive; but, does not have the toxicity or other drawbacks that LA suffers from. In spite of this, DBX-1 has made little progress in replacing LA, due to issues with its production.

Typically DBX-1 is prepared from sodium 5-nitrotetrazolate (NaNT), a compound that has been used as a precursor to other explosives which are produced on large scale, including tetraamine-cis-bis(5-nitrotetrazolato)cobalt(III) perchlorate (BNCP), and mercuric nitrotetrazolate. The synthesis of NaNT and subsequently DBX-1 is shown in Scheme 1, below,

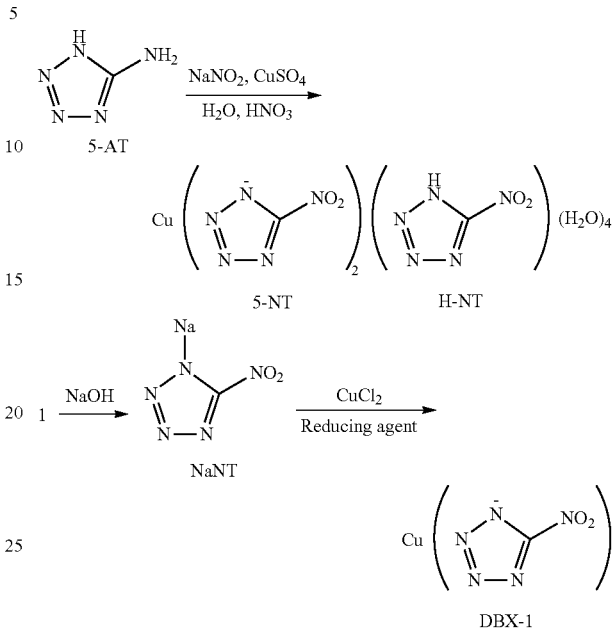

This synthesis of the NaNT was first disclosed by von Herz in 1937, wherein 5-aminotetrazole (5-AT) is first converted to 5-nitrotetrazole (5-NT) by means of a Sandmeyer reaction. The product precipitates from the reaction mixture as 1 (or Complex 1 or intermediate Complex 1), i.e. a copper(II) complex sometimes referred to as the 'acid copper salt' of 5-NT. Von Herz reported its composition as $Cu(H-NT)(NT)_2(OH_2)_4$. This material is a gelatinous green solid that is isolated by a tedious filtration. In 1978, Gilligan and Kamlet in U.S. Pat. No. 4,093,623 disclosed that this filtration became much easier using modified conditions for the Sandmeyer reaction. Specifically, dosing 5-AT in dilute nitric acid instead of dilute sulfuric acid as originally reported led to a dramatic reduction in the amount of time required for the isolation and washing of 1. Gilligan and Kamlet also eliminated "microdetonations" that accompanied dosing 5-AT using the von Herz procedure. These microdetonations were postulated to be due to gaseous nitrous acid reacting with the 5-AT to generate the diazonium species before mixing with the solution containing the catalyst. Without a catalyst present, this highly unstable material would decompose rapidly. Gilligan and Kamlet solved this problem by adding a small quantity of a copper (II) salt, $CuSO_4$, to the solution of 5-AT. This catalyzed the reaction of the diazonium species before it could accumulate and detonate and this procedure is widely used today.

Looking more closely at the present typical process, i.e. the prior art method, the nitro group in 5-NT is installed by a Sandmeyer reaction of 5-aminotetrazole, accomplished by dosing a solution of 5-AT to a mixture containing sodium nitrite and a copper(II) catalyst. This converts 5-AT to 5-NT, which precipitates from the reaction mixture as complex 1, a gelatinous solid. When performing this reaction, the dose solutions of certain concentrations of 5-AT in nitric acid resulted in the nitrate salt of 5-AT precipitating in the dosing lines. 5-AT nitrate is an impact-sensitive explosive reported to melt with violent decomposition at ca. 170° C. In addition to the safety concerns in having this energetic material accumulate in the dosing lines, solid 5-AT nitrate being dosed to the copper sulfate/sodium nitrite solution could result in the precipitation of copper(II) complexes of 5-AT. If these complexes precipitate from solution at this point in the reaction, they would be isolated along with the copper (II) 5-NT Complex 1. As Complex 1 is converted to the NaNT, the copper(II) 5-AT complexes would be converted back to free 5-AT and remain in solution as an impurity, making additional purification steps necessary before the NaNT could be used to produce DBX-1—as any free 5-AT will inhibit the production of DBX-1.

Further, in the typical prior art method detailed above, Complex 1 is a sensitive explosive when dry, and manipulating this material presents hazards to operators, especially as the production scale increases. Again, typically, in a second step, 1 is manually removed from the filter and charged to a reactor containing water. The resulting slurry is treated with aqueous sodium hydroxide, leading to the precipitation of copper(II) oxide, which is removed by filtration, leaving a solution of sodium 5-nitrotetrazolate (NaNT). The resulting solutions of NaNT typically contain a significant amount of residual 5-AT as an impurity (ca. 5% by weight of total dissolved species)—as stated above, such free 5-AT inhibits the subsequent production of DBX-1. So, to purify this material for conversion to transition metal 5-NT complexes, NaNT is typically isolated as its dihydrate, which becomes extremely sensitive if it is allowed to convert to the anhydrous form in dry air. This purification adds another operation to the procedure, adding cost and complexity to the process, and further increasing operator exposure to sensitive energetic solids.

The chemistry involved in the conversion of NaNT to DBX-1 is known in the art. The particulars of this process where disclosed in a paper by John W. Fronabarger et al, published in Propellants, Explosives, Pyrotechnics, Vol. 36, pages 541-550, 2011 and in U.S. Pat. No. 8,523,989, granted to Fronabarger et al, on Sep. 3, 2013.

Thus there is a need in the art for a synthesis of NaNT that can be converted to DBX-1 without any 5-AT contamination, such that no unsafe and inefficient purification is required to remove such a 5-AT contaminant that will inhibit the production of DBX-1. Plus, there is a need to avoid removing and handling the key intermediate Complex 1, which in the currently/prior art process requires removal from the reactor to be filtered and washed—a significant safety issue.

SUMMARY OF INVENTION

The present invention address the above stated needs in the art for a synthesis process for copper(I) 5-nitrotetrazolate (aka "DBX-1") by modifying the prior art process by: (1) using a sulfuric acid solution to dissolve and retain in solution all 5-AT, so that the Complex 1 contains no significant amount of 5-AT and therefore the NaNT produced from such Complex 1 does not require purification, as no 5-AT salt remains to later inhibit the production of the desired DBX-1; and (2) using a reactor with an internal filter to enable isolation of intermediate Complex 1, perform washes of that material, and convert it to NaNT—all without removing the intermediate Complex 1 from the reactor. Further, the NaNT solution produced according to the present invention can be safely stored, or used directly in a second reactor to prepare the desired DBX-1.

Therefore, the present inventive process of synthesizing DBX-1 from 5-AT is:

(a) mixing an effective quantity of 5-aminotetrazole (5-AT) with an effective quantity of sulfuric acid ($H_2SO_4$); a first copper source, such as copper(II) sulfate ($CuSO_4$); water ($H_2O$); and a nitrite source, such as sodium nitrite ($NaNO_2$); to react and form a Complex 1 precipitate, which is a copper (II) complex of 5-NT;

(b) mixing the Complex 1 precipitate with an effective quantity of sodium hydroxide solution to react and form a solution containing sodium 5-nitrotetrazolate (NaNT), which solution is substantially free of any 5-AT; and (c) mixing the NaNT solution with an effective quantity of a second copper source, such as copper(II) chloride ($CuCl_2$) and an effective quantity of a reducing agent (e.g. sodium ascorbate) to react and form the desired DBX-1.

More specifically, as stated above, U.S. Pat. No. 4,093,623 disclosed that modifying the conditions for the Sandmeyer reaction by dosing the initial 5-AT ingredient in dilute nitric acid instead of dilute sulfuric acid, as originally reported, led to a dramatic reduction in the amount of time required for the isolation and washing of 1. This elimination of any use of sulfuric acid led to a much more efficient means of producing the desired sodium 5-nitrotetrazolate (NaNT), which as stated above is a precursor to other explosives, including tetraamine-cis-bis(5-nitrotetrazolato) cobalt(III) perchlorate (BNCP), and mercuric nitrotetrazolate. However, surprisingly, the present invention by using a dilute sulfuric acid, versus the previously universally accepted dilute nitric acid, significantly more solubilizes the Sandmeyer reaction's starting ingredient 5-AT (again, 5-aminotetrazole), i.e. about 3 times better solubilization with dilute sulfuric acid than the use of dilute nitric acid—such that the 5-AT is fully consumed in the Sandmeyer reaction and none remains to inhibit the desired conversion of the Complex 1 to DBX-1.

Further, as stated above, the use of an internal filter in the agitated reaction vessel avoids the need to remove the Complex 1 material from the reactor to be filtered and washed—which is a critical improvement. Complex 1 is a sensitive explosive material and avoiding the handling involved in the prior art removal from the reactor, filtration and washing and then recharging into a subsequent reactor for conversion to NaNT is a significant safety improvement. Further, avoiding such removal of the Complex 1 precipitate is also a time and expense saving step. Finally, use of the internal filter can also preferably be made at the end of the process—because the DBX-1 crystals must be separated from the wash liquid—and the internal filter can be used for this step. The internal filter can preferably be a 2 micron filter made of stainless steel filter or a similar inert material.

Further features and advantages of the present invention will be set forth in, or apparent from, the drawings and detailed description of preferred embodiments thereof which follows.

BRIEF DESCRIPTION OF THE DRAWING

A more complete understanding of the present invention disclosure may be realized by reference to the accompanying drawings in which:

FIG. 2 is a schematic representation of the present invention method steps for the conversion of NaNT to DBX-1.

DETAILED DESCRIPTION OF INVENTION

As detailed above, the present inventive method provides a more effective, safer and more cost effective method of producing DBX-1 (copper(I) 5-nitrotetrazolate) from the starting material 5-AT (5-aminotetrazolate)—wherein there is no residual 5-AT remaining at the final steps to inhibit the DBX-1 crystallization/production. Further, the present inventive method utilizes an internal filter, to avoid the removal and required wash of the acid copper salt intermediate (Complex 1) from the initial reactor—thereby avoiding a significant risk, as Complex 1 is itself a sensitive energetic material. And, by such use of a jacketed agitated reactor with an internal filter—all of the steps in the present inventive method can be carried out in one reactor—thereby making for a more efficient process than that of the prior art (where multiple reactors were required). However, of course, the Complex 1 and or NaNT intermediates can be stored and subsequently used in later reactions—to produce the desired DBX-1 or another final explosive material.

Figure 1:
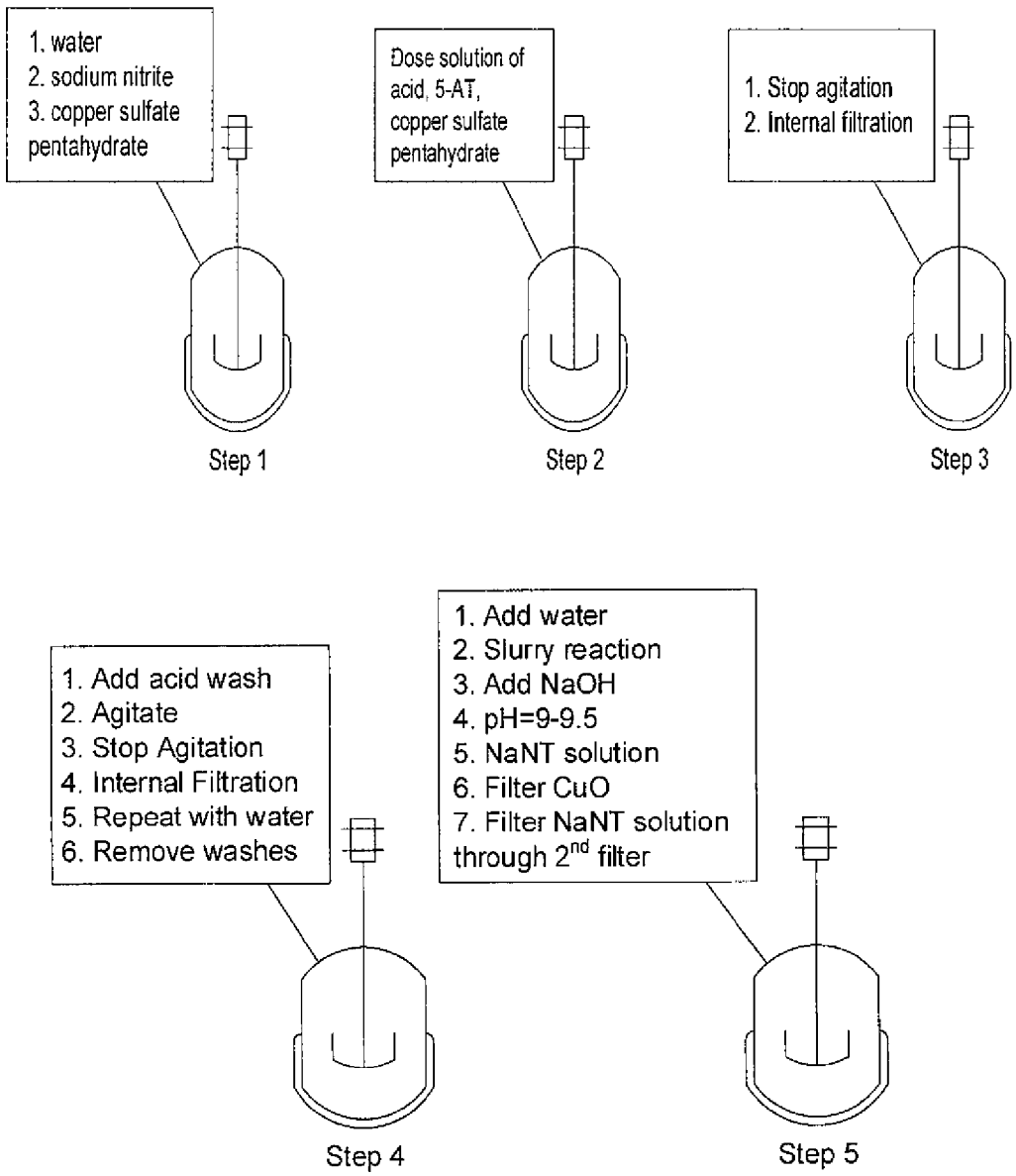
FIG. 1 is a schematic representation of the present invention method steps for the conversion of 5-AT to NaNT.
Figure 3:
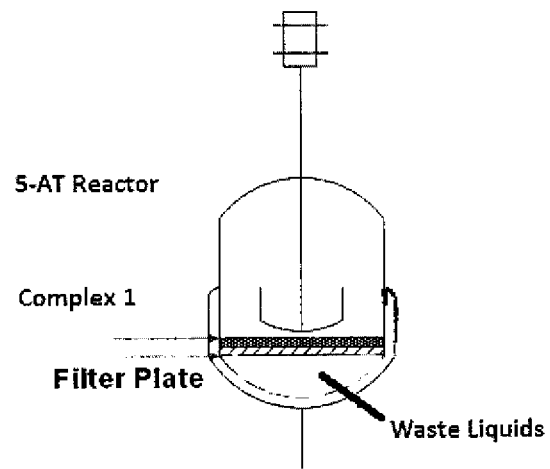
FIG. 3 is schematic representation of the present invention showing the method step involving the internal filtration of Complex 1.

While the present inventive method of producing the desired DBX-1 was carried out in a bench top scale process, wherein a typical 600-mL jacketed filter reactor, fitted with a glass radial flat-bladed turbine, temperature probe, pH probe, and a 20 µm filter disc or plate (though a 1 to 20 µm filter disc or plate is useful)—which may be manufactured of stainless steel or other compatible material—such method can easily be scaled-up to economic large scale manufacturing. In this particular bench top process, reagent doses with specified dosing rates were performed by using a peristaltic pump to dose reagent solutions from a bottle on a balance. The pumping rate was controlled gravimetrically to achieve the desired dosing rate. As schematically illustrated in FIG. 1, Step 1, a first solution containing (i) water (117 g), (ii) copper(II) sulfate pentahydrate (21.4 g, 0.0855 mol), and (iii) sodium nitrite (53.6 g, 0.776 mol) was charged to the reactor and the temperature of the reaction mixture was controlled to 10° C. As schematically illustrated in FIG. 1, Step 2, a second relatively dilute sulfuric acid and 5-AT solution, and also with copper sulfate pentahydrate salt ($CuSO_4 \cdot 5H_2O$) as a catalyst was added—more specifically—(i) water (272 g), (ii) 98% sulfuric acid (19.5 g, 0.195 mol), (iii) 5-aminotetrazole (16.5 g, 0.194 mol), and (iv) copper(II) sulfate pentahydrate (0.775 g, 0.0031 mol) was dosed to the reactor at a rate of 2.1 g/min, keeping the reaction temperature below 14° C. Preferably, an additional quantity of more concentrated sulfuric acid solution was added to the reaction—this third solution contained (i) water (20.5 g) and (ii) 98% sulfuric acid (21.3 g, 0.213 mol) was dosed to the reactor at a rate of 1.3-2.6 g/min, keeping the reaction temperature is preferably below about 15° C. The resulting reaction mixture was stirred for 1 hour—after which the liquid is drained off and the desired Complex 1 precipitate is collected on the preferably 10-20 µm filter plate or disc (see FIG. 1, Step 3, and FIG. 3). Diatomaceous earth (19.3 g) is preferably added in one portion, prior to the filtration, to aid in therein and stirred into the reaction mixture before stirring was stopped. Also, preferably, the reactor drain was connected to a side-arm vacuum flask (not shown in the FIG. 1, Step 3, or FIG. 3 schematics).

Importantly, the precipitated Complex 1 solids collected on the filter plate (FIG. 3) are extremely sensitive energetic materials when dry—therefore these solids should not be allowed to dry. And, if filter breakthrough is observed and Complex 1 solids pass around the filter, closing the drain valve could compress these materials and result in energetic initiation. This could lead to equipment damage and injury. Therefore the drain valve should not be closed until the Complex 1 solids have been washed with a fourth solution containing (i) water (219 g) and (ii) 98% sulfuric acid (24.9 g)—which fourth solution was added to the reactor in a single portion (see FIG. 1, Step 4). The mixture was stirred for five minutes before stirring was stopped and the contents were drained by the same method as detailed above. Next, water (228 g) was added to the reactor, again in a single portion, and the mixture was stirred before stirring was stopped and the contents were drained by the same method as detailed above. The final water wash was repeated until the filtrate, now the desired complex 1 material, had a pH of 1.3—preferably about two additional washes.

As illustrated in FIG. 1, Step 5, the complex 1 material was then converted to NaNT by adding water (282 g) to the reactor containing the filtrate complex 1 material and stirring was resumed to achieve a slurry of green solids. The reaction temperature was increased to 50° C. A 50% (w/w) aqueous solution of sodium hydroxide was dosed in portions to the reaction mixture until the reaction mixture reached a pH between 9.0 and 9.5, preferably about pH 9.1 (9.08 g added, 0.114 mol). During this dose, the green solids suspended in the reaction are replaced by black solids. The reaction temperature was increased to 70° C. The mixture was stirred at this temperature for 1 hour before stirring was stopped and the liquors were drained through the filter by the same procedure as detailed above. The first portion of filtrate (36.4 g) is contaminated with black solids due to a small amount of the material being formed below the filter plate. The second portion (292.3 g) was free of solids. This solution was found to contain 5-NT (6.39% w/w as NaNT dihydrate), nitrite (0.072% w/w), nitrate (0.070% w/w), and sulfate (0.079% w/w)—no 5-AT was not detected. The solution that was free of solids provided the equivalent of 18.7 g of NaNT dihydrate (0.108 mol, 55.7% yield).

Figure 4:
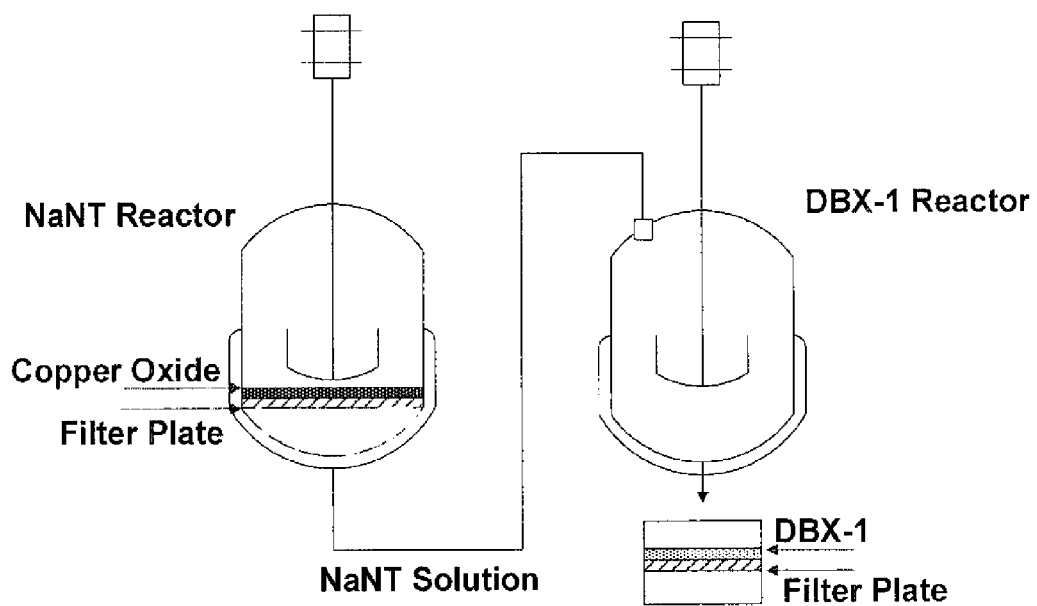
FIG. 4 is schematic representation of the present invention showing the method step involving the internal filtration of the desired DBX-1 product.

As illustrated in FIG. 2, Step 6, the NaNT solution, free of any 5-AT, was then converted to the desired DBX-1 by using a 100-mL reactor which was fitted with a glass pitched-blade impeller, internal temperature probe, and additional probes to monitor particle size and visualize particle morphology (such as a Mettler Toledo FBRM® and PVM®)—the chemistry of this NaNT conversion is known, as stated above. The reactor was charged with DBX-1 seed crystals (22.0 mg) that was suspended in water (35.0 g) and stirring was initiated. The reactor was then charged with an aqueous solution of copper(II) chloride (1 M, 12.2 mL, 12.2 mmol, 1.05 equiv.). The reaction temperature was increased to 90° C. over 30 minutes. And, the reactor was then charged with an aqueous solution of the NaNT (27.0 g, 7.4% w/w 5-NT, 11.6 mmol, 1.00 equiv). This NaNT solution was prepared by blending lots prepared using the 600 mL procedure described above. The solution was not purified prior to use. After the NaNT solution has been added the solution was a clear blue. To this clear blue solution, a syringe pump was set up to dose a 1.0 M aqueous solution of sodium ascorbate (1 M, 0.95 mL, 0.082 equiv.) at a rate of 0.1 mL/min. This addition of the sodium ascorbate caused the clear, blue solution to turn into a turbid, brown suspension of gelatinous solids. After 42 minutes, the solids rapidly transformed into dark red crystalline solids suspended in a clear greenish liquor. At this point, additional 1.0 M aqueous sodium ascorbate was dosed to the reaction mixture (5.36 mL, 0.46 equiv.) at a rate of 0.5 mL/min. After this additional dose of aqueous sodium ascorbate, the reaction mixture consisted of dark red crystalline solids. As illustrated in FIG. 2, Steps 7-8, the stirring was stopped, allowing the solids to settle to the bottom of the reactor—onto an internal filter plate as illustrated in FIG. 4. The liquor was carefully drawn out using a peristaltic pump. A water (25 mL) rinse was added to the reactor, and the mixture was stirred until the mixture reaches at least 85° C. At that point, the stirring is stopped, and the solids were again allowed to settle onto the internal filter plate. The liquor was removed, again using a peristaltic pump. This water rinse was repeated one additional time, by adding a final portion of water (25 mL) to the solids and the mixture was stirred until the reaction temperature reaches at least 85° C.

After the two water rinse steps detailed above, and as illustrated in FIG. 2, Step 9 and FIG. 4, the reactor lid and probes are removed, and the reactor contents were transferred to a Büchner funnel fitted with a filter paper disc. The isolated solids were rinsed twice with 2-propanol and transferred to a conductive container for storage. The solids where then dried. After drying, the container had a net weight of 1.7 g DBX-1 (85% yield). PXRD pattern matches the predicted pattern for DBX-1 with no additional peaks other than those due to the sample holder, $T_{onset}$=302.8° C. (5° C./min, 0.315 mg sample) by DSC.

Although the invention has been described above in relation to preferred embodiments thereof, it will be understood by those skilled in the art that variations and modifications can be effected in these preferred embodiments without departing from the scope and spirit of the invention as claimed below.

What is claimed is:

1. A method of manufacture of copper(I) 5-nitrotetrazolate (DBX-1) comprising:
   a) mixing an effective quantity of 5-aminotetrazole (5-AT) with an effective quantity of sulfuric acid ($H_2SO_4$), a first copper source, water ($H_2O$), and a nitrite source to react and form a Complex 1 precipitate, which is the acid salt of 5-NT (Cu(H—NT)(NT)$_2$(OH$_2$)$_4$);
   b) mixing an effective quantity of the Complex 1 with an effective quantity of sodium hydroxide solution to react and form a solution containing sodium 5-nitrotetrazolate (NaNT), which is filtered to remove insoluble solids, leaving a solution containing NaNT, but that is substantially free of any 5-AT; and
   c) mixing an effective quantity of this NaNT solution that has not been purified other than to remove insoluble solids with an effective quantity of a second copper source and an effective quantity of a reducing agent to react and form the desired DBX-1.

2. The method of manufacture of copper(I) 5-nitrotetrazolate (DBX-1) of claim 1, wherein the first copper source is copper(II) sulfate ($CuSO_4$) and the second copper source is copper(II) chloride ($CuCl_2$) and the nitrite source is sodium nitrite ($NaNO_2$).

3. The method of manufacture of copper(I) 5-nitrotetrazolate (DBX-1) of claim 2, wherein the temperature of the reaction of 5-aminotetrazole (5-AT) with an effective quantity of sulfuric acid ($H_2SO_4$), copper(II) sulfate ($CuSO_4$), water ($H_2O$), and sodium nitrite ($NaNO_2$) to form a Complex 1 is maintained at below about 15 degrees C.

4. The method of manufacture of copper(I) 5-nitrotetrazolate (DBX-1) of claim 2, wherein diatomaceous earth is added to the mixture of 5-aminotetrazole (5-AT) with sulfuric acid ($H_2SO_4$), copper(II) sulfate ($CuSO_4$), water ($H_2O$), and sodium nitrite ($NaNO_2$), to aid in the precipitation of the Complex 1 precipitate.

5. The method of manufacture of copper(I) 5-nitrotetrazolate (DBX-1) of claim 1, wherein the Complex 1 precipitate is washed with a series of water and sulfuric acid solutions and with a final water only solution.

6. The method of manufacture of copper(I) 5-nitrotetrazolate (DBX-1) of claim 1, wherein the temperature of the reaction of the Complex 1 with the sodium hydroxide solution to form a solution containing sodium 5-nitrotetrazolate (NaNT) is maintained at an elevated temperature of at least 50 degrees C.

7. The method of manufacture of copper(I) 5-nitrotetrazolate (DBX-1) of claim 2, wherein the mixing of the NaNT solution with copper(II) chloride ($CuCl_2$) to react and form the desired DBX-1 is seeded with DBX-1 crystals.

8. The method of manufacture of copper(I) 5-nitrotetrazolate (DBX-1) of claim 2, wherein the mixing of the NaNT solution with copper(II) chloride ($CuCl_2$) to react and form the desired DBX-1 is maintained at an elevated temperature of up to about 85 to about 90 degrees C.

9. The method of manufacture of copper(I) 5-nitrotetrazolate (DBX-1) of claim 2, wherein in the formation of the Complex 1 precipitate—in the reaction of 5-aminotetrazole (5-AT) with sulfuric acid ($H_2SO_4$), copper(II) sulfate ($CuSO_4$), water ($H_2O$), and sodium nitrite ($NaNO_2$)—the precipitate is captured onto a filter plate located within a reactor in which this reaction occurs.

10. The method of manufacture of copper(I) 5-nitrotetrazolate (DBX-1) of claim 9, wherein the filter plate provides 1 to 20 µm filtration.

11. The method of manufacture of copper(I) 5-nitrotetrazolate (DBX-1) of claim 1, wherein the Complex 1 is mixed with sodium hydroxide solution to react and form a solution containing sodium 5-nitrotetrazolate (NaNT) in a reactor—the solution is separated from the waste solids formed in this reaction by a filter plate internal to the reactor—which filter plate provides 1 to 20 µm filtration.

12. The method of manufacture of copper(I) 5-nitrotetrazolate (DBX-1) of claim 1, wherein the reducing agent is sodium ascorbate.

* * * * *